(12) United States Patent
Chao et al.

(10) Patent No.: US 7,257,187 B2
(45) Date of Patent: Aug. 14, 2007

(54) METHODS AND APPARATUS FOR CALIBRATING CT X-RAY BEAM TRACKING LOOP

(75) Inventors: Edward Henry Chao, Oconomowoc, WI (US); Thomas Louis Toth, Brookfield, WI (US); Maryam Shaukat Hameed, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 201 days.

(21) Appl. No.: 11/124,331

(22) Filed: May 6, 2005

(65) Prior Publication Data
US 2006/0251210 A1    Nov. 9, 2006

(51) Int. Cl.
*H05G 1/30*    (2006.01)
(52) U.S. Cl. ....................................................... 378/19
(58) Field of Classification Search .................. 378/19
See application file for complete search history.

(56) References Cited

U.S. PATENT DOCUMENTS

| 6,327,331 | B1 | 12/2001 | Toth et al. |
| 6,359,958 | B2 | 3/2002 | Toth |
| 6,370,218 | B1 | 4/2002 | Toth et al. |
| 6,385,279 | B1 | 5/2002 | Toth et al. |
| 6,411,677 | B1 | 6/2002 | Toth et al. |
| 6,917,665 | B2 * | 7/2005 | Nakanishi et al. ............ 378/19 |

* cited by examiner

*Primary Examiner*—Edward J. Glick
*Assistant Examiner*—Thomas R. Artman
(74) *Attorney, Agent, or Firm*—Armstrong Teasdale LLP

(57) ABSTRACT

A method for determining tracking control parameters for positioning an x-ray beam of a computed tomography imaging system, the imaging system including a movable collimator positionable in steps and a detector array including a plurality of detector elements arranged in rows and channels, the rows extending from a detector A-side to a detector B-side. The method includes determining a detector A-side and a detector B-side target beam penumbra position, computing a plurality of Z-ratio curves corresponding to different detector rows and detector channels, and comparing the Z-ratio curves at the detector A-side and detector B-side target beam positions to determine the optimal Z-ratio curve and corresponding detector channels and rows for controlling the X-ray beam positioning.

21 Claims, 5 Drawing Sheets

```
                                                    ┌─ 18
```

Determining a detector A-side and a detector B-side target beam position — 102

Computing a plurality of Z-ratio curves corresponding to different detector rows and detector channels. — 104

Comparing the Z-ratio curves at the detector A- side and detector B-side target beam positions to determine an optimal Z-ratio curve and corresponding detector channels and rows for controlling the X-ray beam positioning. — 106

FIG. 4

METHODS AND APPARATUS FOR CALIBRATING CT X-RAY BEAM TRACKING LOOP

BACKGROUND OF THE INVENTION

This invention relates generally to computed tomography (CT) imaging and, more particularly, to methods and apparatus for selecting detector channels to facilitate optimizing the reliability of CT x-ray beam tracking.

In a multi-slice CT system, movement of an x-ray beam penumbra over detector elements having dissimilar response functions can cause signal changes resulting in image artifacts. Opening system collimation to keep detector elements in the x-ray beam umbra can prevent artifacts but increases patient dosage. Accordingly, at least one known CT system utilizes a closed-loop z-axis tracking system to position the x-ray beam relative to a detector array.

For example, in at least one known CT imaging system, the X-ray collimator assembly includes movable cams that are configured to track the focal spot position and thereby more accurately position the X-ray beam on the active elements of the multi-slice detector. Specifically, at least one known CT system detects the X-ray beam profile on one end of the detector and utilizes this information to adjust the cam positions. Whereas another known CT system detects the X-ray beam profile on both ends of the detector, and utilizes this information to adjust the cam positions.

Using both ends of the detector improves the ability to position the X-ray beam for situations when the beam profile does not move rigidly across the detector. However, both systems become less reliable when the detector, the collimator, and the X-ray focal spot are not well aligned. For example, if the X-ray tube is not positioned properly, the X-ray beam will be uniformly displaced toward one side of the detector, i.e., either the A-side or the B-side. Moreover, if the X-ray tube is properly aligned, the ends of the collimator and detector may remain skewed with respect to one another and the beam profile will appear skewed. Mis-alignment between the X-ray tube, the collimator and/or the detector may affect the measurement of the Z-ratio, R, used in the tracking control loop. The Z-ratio, as used herein, is defined a ratio of a detector outer row signal to a detector inner row signal, for a set of detector elements at one or both ends of the detector. The Z-ratio is generally useful when the detector outer rows sample the penumbra, i.e. the drop-off in intensity at the edges of the X-ray beam. Therefore, if the signals received from the detector outer rows are in the umbra, i.e., the uniform intensity region, of the beam, the Z-ratio will approach a constant value and cannot be used to reliably determine the beam position.

BRIEF SUMMARY OF THE INVENTION

In one aspect, a method for determining tracking control parameters for positioning an x-ray beam of a computed tomography imaging system is provided. The imaging system includes a movable collimator positionable in steps and a detector array including a plurality of detector elements arranged in rows and columns, the rows extending from a detector A-side to a detector B-side. The method includes determining a detector A-side and a detector B-side target beam penumbra position, computing a plurality of Z-ratio curves corresponding to different detector rows and detector channels, and comparing the Z-ratio curves at the detector A-side and detector B-side target beam penumbra positions to determine the optimal Z-ratio curve and corresponding detector channels and rows for controlling the X-ray beam positioning.

In another aspect, a Computed Tomographic (CT) imaging system is provided. The CT imaging system includes a movable collimator positionable in steps, a detector array comprising a plurality of detector elements arranged in rows and columns, the rows extending from a detector A-side to a detector B-side, and a computer coupled to the collimator and the detector array. The computer is configured to determine a detector A-side and a detector B-side target beam penumbra position, compute a plurality of Z-ratio curves corresponding to different detector rows and detector channels, and compare the Z-ratio curves at the detector A-side and detector B-side target beam penumbra positions to determine the optimal Z-ratio curve and corresponding detector channels and rows for controlling the X-ray beam positioning.

In a further aspect, a machine readable medium having recorded thereon is provided. The machine readable medium is installed on a CT imaging system including a movable collimator positionable in steps, and a detector array including a plurality of detector elements arranged in rows and columns, the rows extending from a detector A-side to a detector B-side. The machine readable medium configured to instruct a processor to determine a detector A-side and a detector B-side target beam penumbra position, compute a plurality of Z-ratio curves corresponding to different detector rows and detector channels, and compare the Z-ratio curves at the detector A-side and detector B-side target beam penumbra positions to determine the optimal Z-ratio curve and corresponding detector channels and rows for controlling the X-ray beam positioning.

BRIEF DESCRIPTION OF THE DRAWINGS

FIG. 4 is a flow diagram of a method for calibrating tracking loop parameters;

DETAILED DESCRIPTION OF THE INVENTION

Figure 1:
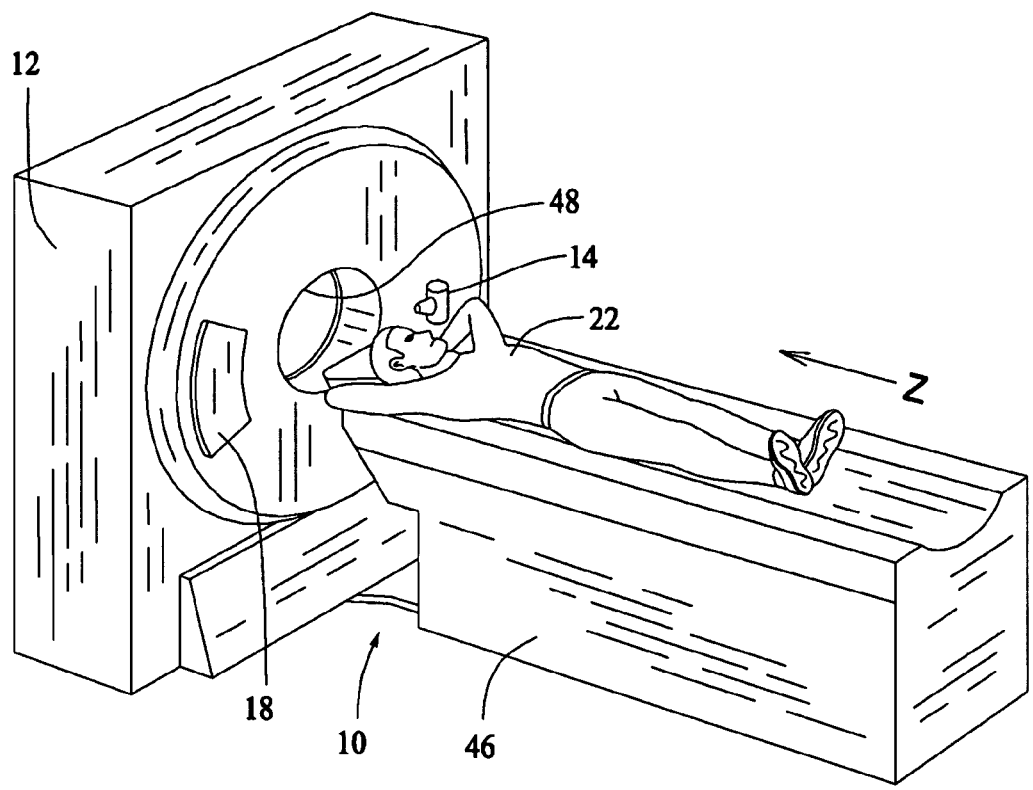
FIG. 1 is a pictorial view of a CT imaging system.

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as the filtered backprojection technique. This process converts the attenuation measurements from a scan into integers called "CT numbers" or "Hounsfield units" (HU), which are used to control the brightness of a corresponding pixel on a display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two-dimensional slice taken through the object.

To further reduce the total acquisition time, multi-slice CT has been introduced. In multi-slice CT, multiple rows of projection data are acquired simultaneously at any time instant. When combined with helical scan mode, the system generates a single helix of cone beam projection data. Similar to the single slice helical weighting scheme, a method can be derived to multiply the weight with the projection data, prior to the filtered backprojection algorithm.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 2:
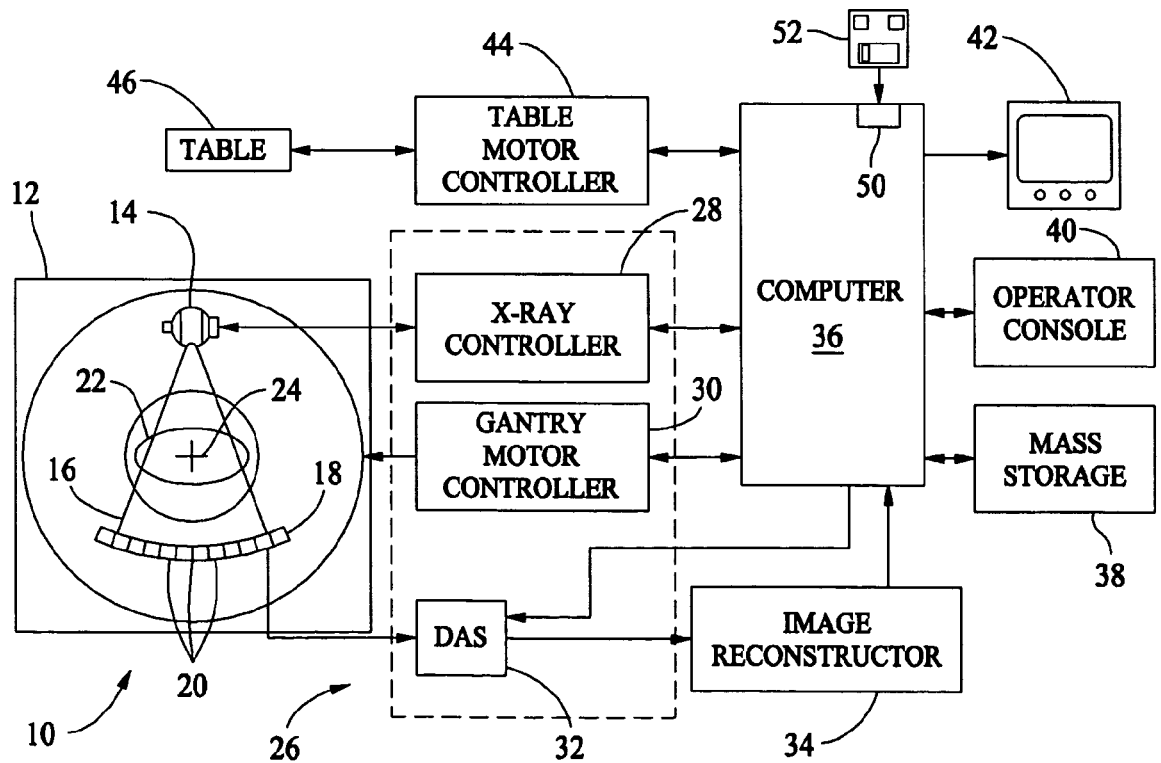
FIG. 2 is a block schematic diagram of the system illustrated in FIG. 1.

Referring to FIGS. 1 and 2, a multi-slice scanning imaging system, for example, a Computed Tomography (CT) imaging system 10, is shown as including a gantry 12 representative of a "third generation" CT imaging system. Gantry 12 has an x-ray tube 14 (also called x-ray source 14 herein) that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22 between array 18 and source 14. Each detector element 20 produces an electrical signal that represents the intensity of an impinging x-ray beam and hence can be used to estimate the attenuation of the beam as it passes through object or patient 22. During a scan to acquire x-ray projection data, gantry 12 and the components mounted therein rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan.

Rotation of components on gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of components on gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a storage device 38. Image reconstructor 34 can be specialized hardware or computer programs executing on computer 36.

Computer 36 also receives commands and scanning parameters from an operator via console 40 that has a keyboard. An associated display 42, for example, a cathode ray tube or other suitable display device, allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment, computer 36 includes an instruction reading or receiving device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or another digital source such as a network or the Internet, as well as yet to be developed digital means. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. Although the specific embodiment mentioned above refers to a third generation CT system, the methods described herein equally apply to fourth generation CT systems (stationary detector—rotating x-ray source) and fifth generation CT systems (stationary detector and x-ray source). Additionally, it is contemplated that the benefits of the invention accrue to imaging modalities other than CT. Additionally, although the herein described methods and apparatus are described in a medical setting, it is contemplated that the benefits of the invention accrue to non-medical imaging systems such as those systems typically employed in an industrial setting or a transportation setting, such as, for example, but not limited to, a baggage scanning system for an airport or other transportation center.

Figure 3:
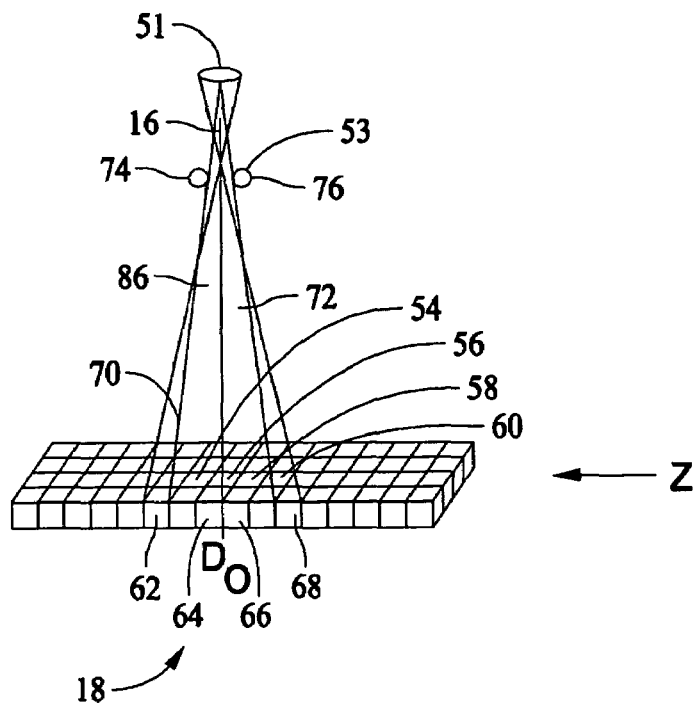
FIG. 3 is a schematic view of a portion of the CT imaging system shown in FIG. 1.

In one embodiment, and as shown in FIG. 3, x-ray beam 16 emanates from a focal spot 51 of x-ray source 14 (shown in FIG. 2). X-ray beam 16 is collimated by a collimator 53, and collimated beam 16 is projected toward detector array 18. Detector array 18 is fabricated in a multi-slice configuration and includes detector element rows 54, 56, 58 and 60 for projection data collection. A plane 86, generally referred to as the "fan beam plane", contains the centerline of focal spot 51 and the centerline of beam 16. Fan beam plane 86 is illustrated in FIG. 3 as being aligned with a centerline $D_0$ of detector array 18, although fan beam plane 86 will not always be so aligned. In the exemplary embodiment, detector element rows 62, 64, 66 and 68 serve as z-position detectors for determining a z-axis position of x-ray beam 16. In one embodiment, detector rows 62, 64, 66, and 68 are rows of detector array 18. Outer rows 62 and 68 are selected to be at least substantially within a penumbra 70 of beam 16, whereas inner rows 64 and 66 are selected to be at least substantially within an umbra 72 of beam 16. "At least substantially within" means either entirely within or at least sufficiently within so that outer row 62 and 68 signal intensities depend on an x-ray beam position and inner row 64 and 66 signal intensities provide references against which outer row signals are compared. In one embodiment, collimator 53 includes tapered cams 74 and 76. (Where it is stated herein that a cam "has a taper," it is not intended to exclude cams having a taper of zero unless otherwise stated.) X-ray controller 28 controls positioning of cams 74 and 76. Each respective cam, 74 and 76, can be independently positioned to alter the position and width of x-ray umbra 72 relative to an edge (not shown) of detector array 18.

FIG. 4 is a flowchart illustrating an exemplary method 100 of calibrating imaging system 10 to facilitate reducing an x-ray dosage delivered to object 22, such as a patient. In the exemplary embodiment, method 100 includes determining 102 a detector A-side and a detector B-side target beam penumbra position, computing 104 a plurality of Z-ratio curves corresponding to different detector columns or rows, and comparing 106 the Z-ratios at the detector A-side and detector B-side target beam penumbra positions to determine an optimal Z-ratio curve and corresponding detector channels and rows.

Figure 5:
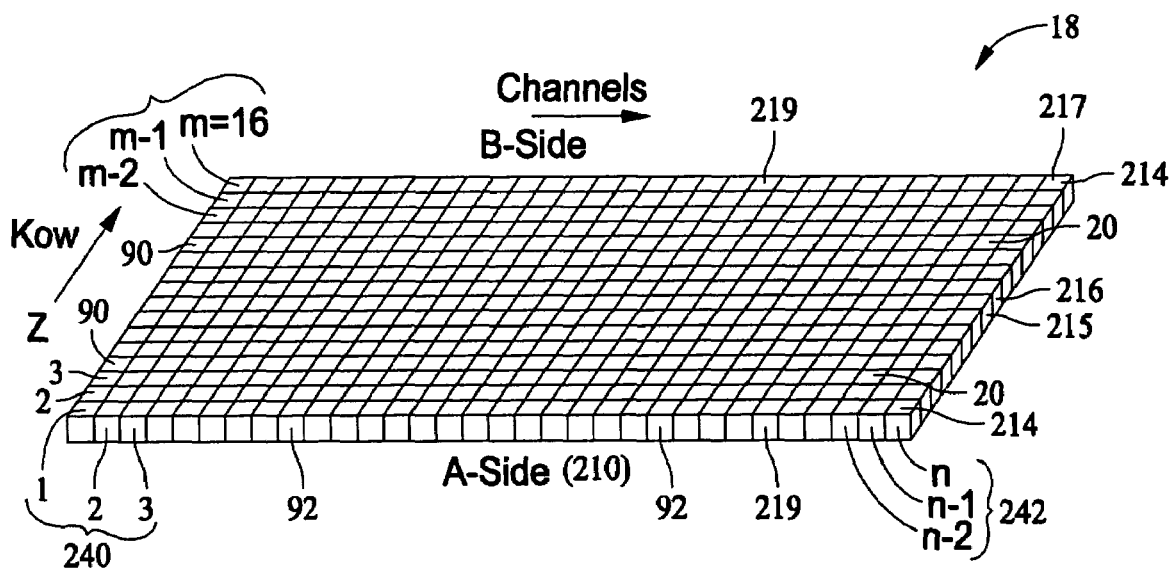
FIG. 5 is a schematic view of a portion of the CT imaging system shown in FIG. 1 showing an embodiment of a z-axis position system of the present invention.

FIG. 5 is an exemplary detector 18 utilized to demonstrate method 100. As shown in FIG. 5, and in the exemplary embodiment, detector array 18 includes m rows 90 and n channels 92, also referred to as columns 92, of detector elements 20 such that detector array 18 has a matrix of m×n detector elements 20. In the exemplary embodiment, m=16 and n=32 such that detector array 18 includes 512 detector elements 20. Although detector array 18 is illustrated as including sixteen rows 90 (m=16) and thirty-two channels 92 (n=32) of detector elements 20, it should be realized that detector array 18 can include any quantity of rows 90 (>=4), and channels 92 without effecting the scope of the invention described herein. Detector array 18 can also be a subset of the entire detector. For example, on a detector with 64 rows and 912 channels, certain modes may require that the X-ray be focused on only the center 16 rows and 912 channels.

In the exemplary embodiment, method 100 is included in an X-ray beam tracking method that is utilized by imaging system 10 to generate the operating parameters used during the real-time control loop calibration as described previously herein. Accordingly, method 100 includes translating the collimator cams 74 and 76 incrementally, i.e. in steps, such that the penumbra 70 of the X-ray beam 16 sweeps across the end-rows 219 of detector array 18. For example, and referring again to FIG. 5, during translation, X-ray beam 16 is positioned at a detector A-side 210, i.e. approximately adjacent to lower numbered rows 1, 2, 3 etc. Collimator cams 74 and 76 are then incrementally shifted such that X-ray beam 16 is shifted toward the higher number rows. More specifically, collimator cams 74 and 76 are incremented such that X-ray beam 16 is shifted to a detector B-side 212, i.e. the higher numbered rows m−2, m−1, m, etc. As used herein, detector A-side 210 refers to a quantity of detector rows that extend from a first or bottom row 214 to a middle row 215 that is positioned approximately in the center of detector 18, and detector B-side refers to a quantity of detector rows that from a row 216 adjacent middle row 215 to a last or top row 217 For example, in the exemplary sixteen row detector described herein, A-side 210 extends from rows 1-8, and B-side 212 extends from rows 9-16. Alternatively, in a thirty-two row detector, A-side 210 extends from rows 1-16, and B-side 212 extends from rows 17-32.

Method 100 also includes determining 104 a first target X-ray beam penumbra position 220 on detector A-side 210 and a second target X-ray beam penumbra position 222 on detector B-side 212 of detector 18. More specifically, and during operation, a ratio of one cam step to the next, i.e. a step ratio, is taken using data from the end-rows 219, i.e. rows 1 and 16 in a sixteen row detector, of the active detector area. For example, in the exemplary embodiment, ends rows 219 include the first detector row and the last detector row, i.e., rows 1 and 16 of a sixteen row detector. In the exemplary embodiment, target beam penumbra positions, 220 and 222, are determined by calculating a plurality of normalized ratios for a detectors row on each of the detector A-side 210 and detector B-side 212, i.e. end rows 219, and finding the smallest collimator aperture having normalized ratios that do not exceed an empirically determined sensitivity function. In the exemplary embodiment, target beam positions 220 and 222 are generated independently of the Z-ratios. Moreover, target beam positions 220 and 222 are selected to facilitate minimizing patient dosage while simultaneously reducing imaging artifacts.

Method 100 also includes calculating a plurality of Z-ratio curves as a function of collimator cam position, the plurality corresponding to different detector channels and rows. Z-ratio as used herein is defined as the ratio of an outer-row of Z-tracking channels over an inner-row of Z-tracking channels. For example, a ratio of outer row 62 and inner row 64, shown in FIG. 3, is used for the Z-ratio calculations on the A-side of the detector, and a ratio of outer row 68 and inner row 66 is used for the Z-ratio calculations on the B-side of the detector. For a first Z-ratio curve, the average of channels 1-12 (low-numbered channels) could be used. For a second Z-ratio curve, the average of channels n-12 to n-1 (high-numbered channels) could be used.

Figure 6:
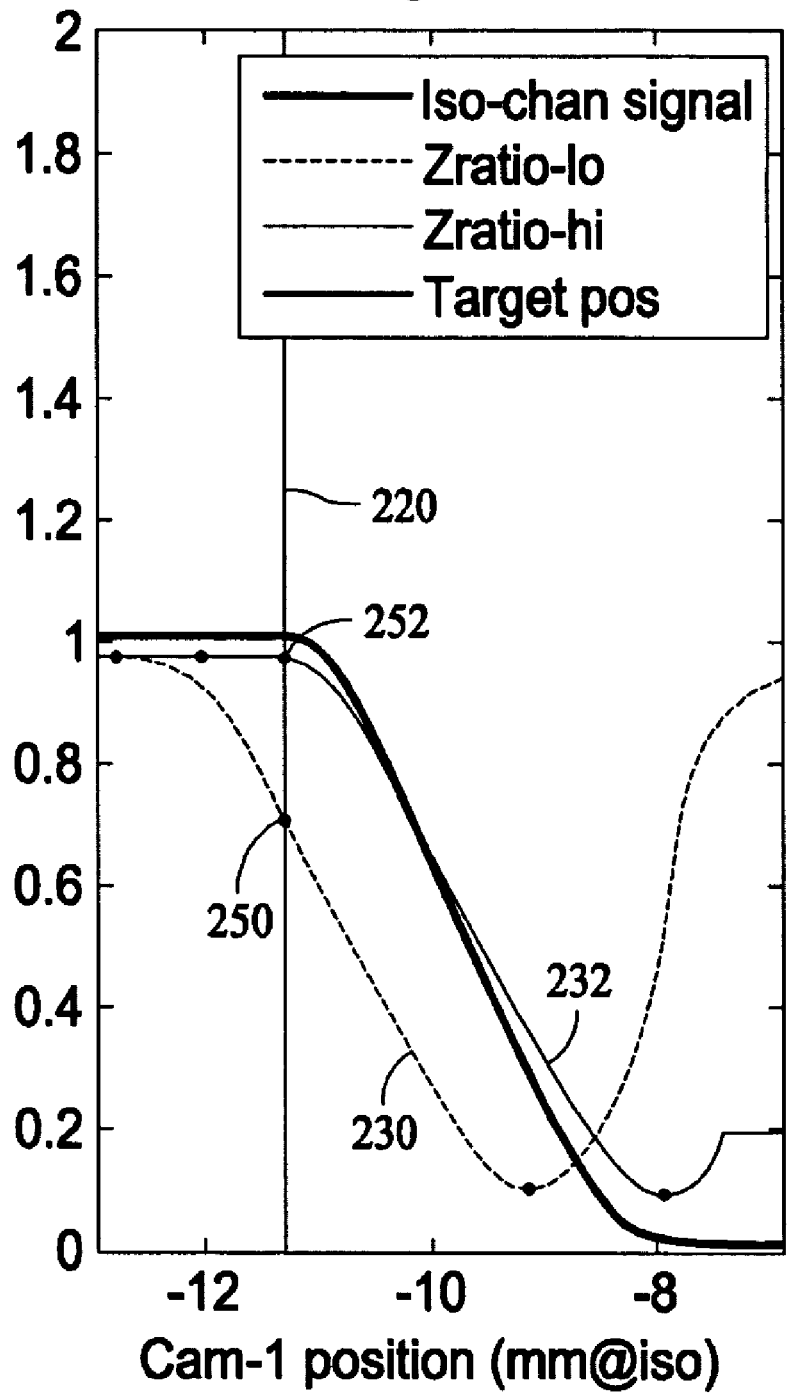
FIG. 6 is a graphical illustration of the method shown in FIG. 4.
Figure 7:
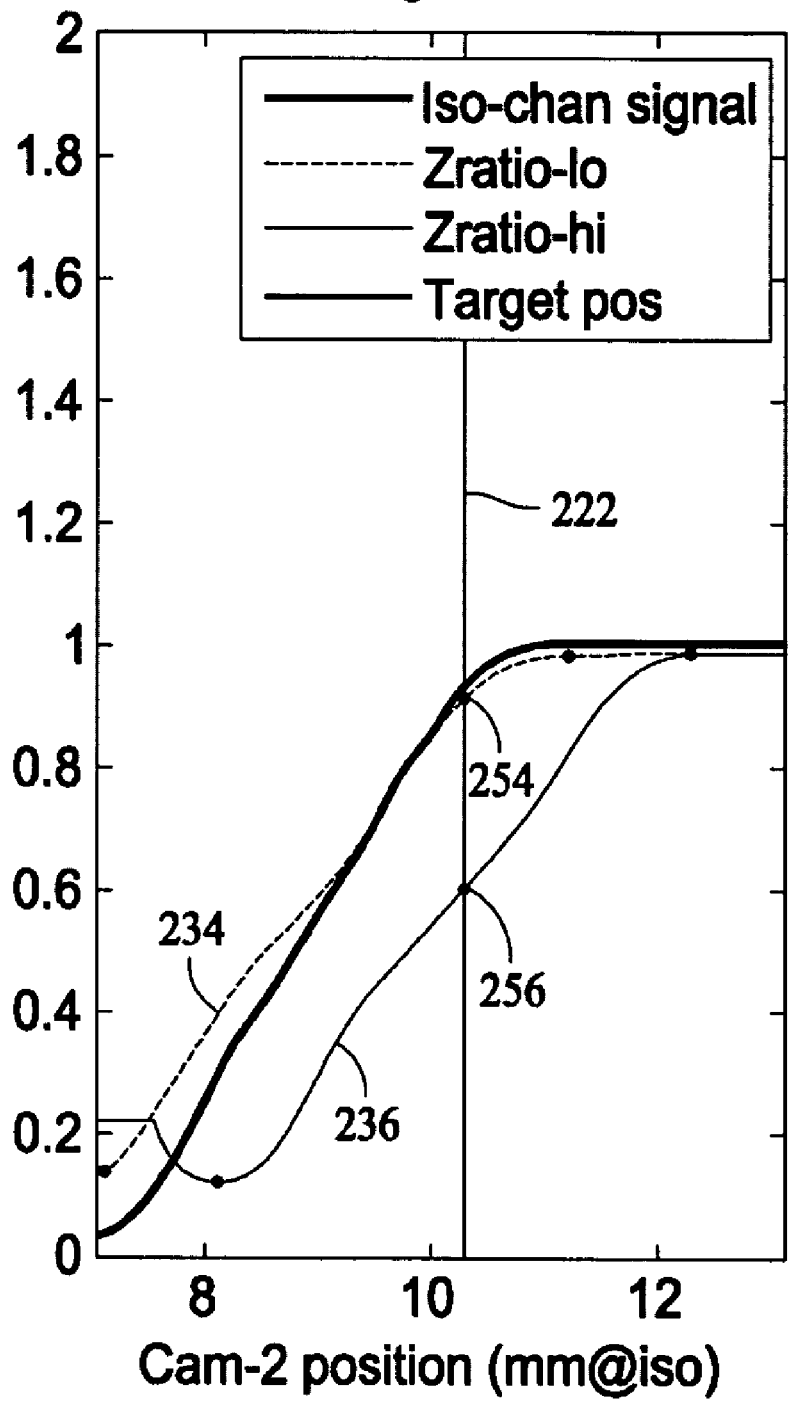
FIG. 7 is a graphical illustration of the method shown in FIG. 4.

A plurality of Z-ratio curves are then generated by calculating the ratios over the range of steps given in the collimator sweep scan. For example, as shown in FIGS. 6 and 7, a first Z-ratio curve 230 (Z-ratio low) is generated for detector A-side 210 using the lower numbered channels, e.g. 1-12, a second Z-ratio curve 232 (Z-ratio high) is generated for detector A-side 210 using the higher numbered channels, e.g. n-12 to n-1, a third Z-ratio curve 234 (Z-ratio low) is generated for detector B-side 212 using the lower numbered channels, e.g. 1-12, and a fourth Z-ratio curve 236 (Z-ratio high) is generated for detector B-side 212 using the higher numbered channels e.g. n-12 to n-1. More specifically, as shown in FIGS. 6 and 7, the Z-ratio curves (230, 232, 234, 236) are calculated for both sides of detector 18 (A-side 210 and B-side 212), corresponding to the bottom row (1) and the top row (16) of the detector shown in FIG. 5.

In the exemplary embodiment, the same detector rows are chosen for the Z-ratios generated using the low numbered channels and the high numbered channels. Therefore, on a well aligned system, Z-ratios curves 230, 232, 234, 236, generated using either the low-channel end or the high-channel end of detector 18, will overlap.

For example, referring to FIGS. 6 and 7, the target beam penumbra positions, 220 and 222, for both the A-side 210 and B-side 212 are graphically illustrated as vertical lines which indicate the target beam penumbra positions determined in method 100. In the exemplary embodiment, method 100 also includes determining a first operating point 250 and a second operating point 252, and then selecting a Z-ratio curve where the operating point, either 250 or 252, has the greatest margin.

For example, as discussed previously herein, the Z-ratio is a ratio of an outer row detector signal to an inner row signal, for a set of detector elements at one or both ends of the detector. The ratio is only useful when the outer row of detectors samples the penumbra (the drop-off in intensity at the edges) of the X-ray beam. If the outer row signal is in the umbra (uniform intensity region) of the beam, the Z-ratio will approach a constant value (usually near unity) and cannot be used to reliably determine the beam position.

Accordingly, method 100 also includes selecting the most reliable Z-ratio curve for each side A-side 210 and B-side 212. For example, in the exemplary embodiment, either curve 230 or 232 is selected for the A-side, and either curve 234 or 236 is selected for the B-side. Selecting the most reliable Z-ratios curves, i.e. the Z-ratio curves with the greatest margin, includes determining the minimum value of the Z-ratio curve (minZratio) for each Z-ratio curve 230, 232, 234, and 236, determining the maximum value of each Z-ratio curve (maxZratio) for each Z-ratio curve 230, 232, 234, and 236, determining the value at an operating point (opZratio), determining a margin for each Z-ratio curve, wherein margin=lesser of (opZratio-minZratio) or (maxZratio-opZratio), and selecting a Z-ratio curve where the operating point, either 250 or 252, has the greatest margin.

For example, referring to FIG. 6, the minimum value of Z-ratio curve 230 (minZratio) is approximately 0.1, the maximum value of Z-ratio curve 230 (maxZratio) is approximately 1.0, and the operating point 250 (opZratio) of Z-ratio curve 230, i.e. the point in which the Z-ratio curve crosses target 220, is approximately 0.7. The margin for Z-ratio curve 230 is the lesser of (0.7-0.1) or (1.0-0.7), i.e. the lesser of 0.6 and 0.3. Accordingly, the margin for Z-ratio curve 230 is 0.3.

Moreover, the minimum value of Z-ratio curve 232 (minZratio) is approximately 0.1, the maximum value of Z-ratio curve 232 (maxZratio) is approximately 1.0, and the operating point 252 (opZratio) of Z-ratio curve 232, i.e. the point in which the Z-ratio curve crosses target 220, is approximately 1.0. The margin for Z-ratio curve 232 is the lesser of (1.0-0.1) or (1.0-1.0), i.e. the lesser of 0.09 and 0.0. Accordingly, the margin for Z-ratio curve 232 is 0.0.

Therefore, operating point 250, has the greatest margin, thus Z-ratio curve 230 would be utilized to position the X-ray beam during normal patient scanning. Although, this example is shown only for detector A-side 210, it should be realized that selecting the most reliable Z-ratios curves is also conducted on detector B-side 212 by determining operating points 254 and 256 as described previously herein, and selecting a Z-ratio, i.e. either curve 234 and 236, where the operating point has the greatest margin. Accordingly, and in the exemplary embodiment, either the lower or higher channels will be chosen for each of the sides (A and B), to position the X-ray beam on the detector.

Described herein, is a method and system for performing a system calibration of a CT imaging system. More specifically, as described herein, either the low-channel or high-channel end of the detector can be utilized to calculate the Z-ratio. Moreover, the methods described herein can also be utilized to optimize which detector rows are used for the Z-ratios. For example, on an exemplary VCT (64-slice) scanner, the Z-ratio is calculated using rows 18A and 1A (18A/1A) for a 32-slice acquisition. It has been observed that when the X-ray tube focal spot is not well aligned, the Z-ratio value at the target point is near the limits for both the high and low channel Z-ratios. Accordingly, the methods described herein add the flexibility to use additional rows, for example, 17A/1A, for calculating the Z-ratios to facilitate improving system reliability, and/or to facilitate reducing the X-ray dose received by a patient.

In some embodiments, the methods described herein are implemented by software, firmware, or by a combination thereof controlling either computer 36, image reconstructor 34, or both. Also, additional z-detector rows can be provided. In such an embodiment, various combinations of z-detector row signals can be used as the inner and outer row signals, thereby becoming identified as such, or a different and/or more elaborate transfer function can be used to determine a beam position.

It should be understood that system 10 is described herein by way of example only, and the invention can be practiced in connection with other types of imaging systems. Furthermore, it will be recognized by those skilled in the art that the calibration system described herein is also useful for other applications which require x-ray beam tracking calibration, such as for object location or sensing of movement.

While the invention has been described in terms of various specific embodiments, those skilled in the art will recognize that the invention can be practiced with modification within the spirit and scope of the claims.

What is claimed is:

1. A method for determining tracking control parameters for positioning an x-ray beam of a computed tomography imaging system, the imaging system including a movable collimator positionable in steps and a detector array including a plurality of detector elements arranged in rows and channels, the rows extending from a detector A-side to a detector B-side, said method comprising:

determining a detector A-side and a detector B-side target beam penumbra position;

computing a plurality of Z-ratio curves corresponding to different detector rows and detector channels;

comparing the Z-ratio curves at the detector A-side and detector B-side target beam penumbra positions to determine the optimal Z-ratio curve and corresponding detector channels and rows for controlling the X-ray beam positioning; and controlling the X-ray beam positioning based on the above determined optimal Z-ratio curve and corresponding detector channels and rows.

2. A method in accordance with claim 1 wherein determining a detector A-side and a detector B-side target beam penumbra position comprises:
obtaining detector samples at a plurality of collimator step positions; and
determining a step-ratio of the signals received from at least one detector A-side row and at least one detector B-side row.

3. A method in accordance with claim 2 further comprising:
generating the target beam positions independently of the Z-ratios by selecting the smallest collimator aperture where the step-ratio does not exceed an empirically determined sensitivity function.

4. A method in accordance with claim 3 further comprising:
generating the target beam penumbra positions on the detector A-side and the detector B-side by comparing the step-ratio to the sensitivity function for the detector A-side end row and the detector B-side end row.

5. A method in accordance with claim 1 wherein computing a plurality of Z-ratio curves corresponding to different detector rows and detector channels comprises:
generating a plurality of Z-ratio curves for the detector A-side and the detector B-side utilizing a plurality of channels and at least one inner and one outer row;
generating a plurality of Z-ratio curves utilizing the detector channel signals measured while the collimator cams and corresponding beam penumbra are stepped across the detector; and
generating a plurality of Z-ratio curves, where each curve is a function of the X-ray beam penumbra position.

6. A method in accordance with claim 5 further comprising:
determining a minimum value for each generated Z-ratio curve;
determining a maximum value for each generated Z-ratio curve; and
determining an operating point for each Z-ratio curve.

7. A method in accordance with claim 6 where determining an operating point for each Z-ratio curve comprises:
determining the point on each Z-ratio curve for which the X-ray beam penumbra position is at the target position.

8. A method in accordance with claim 7 further comprising:
determining a margin for each Z-ratio curve;
selecting a detector A-side Z-ratio curve having the largest margin;
selecting a detector B-side Z-ratio curve having the largest margin; and
utilizing the selected Z-ratio curves and corresponding detector channels and rows to position the collimator cams and X-ray beam during normal patient scanning.

9. A Computed Tomographic (CT) imaging comprising:
a movable collimator positionable in steps;
a detector array comprising a plurality of detector elements arranged in rows and channels, the rows extending from a detector A-side to a detector B-side; and
a computer coupled to said collimator and said detector array, said computer configured to:
determine a detector A-side and a detector B-side target beam position;
compute a plurality of Z-ratio curves corresponding to a plurality of detector rows and channels; and
compare the Z-ratio curves at the detector A-side and detector B-side target beam penumbra positions to determine the optimal Z-ratio curve and corresponding detector channels and rows for controlling the X-ray beam positioning.

10. A system in accordance with claim 9, wherein said computer is further configured to:
obtain detector samples at a plurality of collimator step positions that extend from the detector A-side to the detector B-side; and
determine a step-ratio of the signals received from at least one detector A-side row and at least one detector B-side row.

11. A system in accordance with claim 10, wherein said computer is further configured to:
generate the target beam penumbra positions independently of the Z-ratios by selecting the smallest collimator aperture where the step-ratio does not exceed an empirically determined sensitivity function; and
determine the point on each Z-ratio curve for which the X-ray beam penumbra position is at the target position.

12. A system in accordance with claim 11, wherein said computer is further configured to:
generate the target beam penumbra positions on the detector A-side and the detector B-side by comparing the step-ratio to the sensitivity function for the detector A-side end row and the detector B-side end row.

13. A system in accordance with claim 11 wherein said computer is further configured to:
determine a margin for each Z-ratio curve;
select a detector A-side Z-ratio curve having the largest margin;
select a detector B-side Z-ratio curve having the largest margin; and
utilize the selected Z-ratio curves and corresponding detector channels and rows to position the collimator cams and X-ray beam during normal patient scanning.

14. A system in accordance with claim 9 wherein said computer is further configured to:
generate a plurality of Z-ratio curves for the detector A-side and the detector B-side utilizing a plurality of channels and at least one inner and one outer row;
generate a plurality of Z-ratio curves utilizing the detector channel signals measured while the collimator cams and corresponding beam penumbra are stepped across the detector; and
generate a plurality of Z-ratio curves, where each curve is a function of the X-ray beam penumbra position.

15. A system in accordance with claim 14, wherein said computer is further configured to:
determine a minimum value for each generated Z-ratio curve;
determine a maximum value for each generated Z-ratio curve; and
determine an operating point for each Z-ratio curve.

16. A machine readable medium having recorded, said machine readable medium installed on a CT imaging system including a movable collimator positionable in steps, and a detector array including a plurality of detector elements arranged in rows and channels, the rows extending from a detector A-side to a detector B-side, said machine readable medium configured to instruct a processor to:
determine a detector A-side and a detector B-side target beam position;
compute a plurality of Z-ratios; and
compare the Z-ratio curves at the detector A-side and detector B-side target beam positions to determine the optimal Z-ratio curve and corresponding detector channels and rows for controlling the X-ray beam positioning.

17. A machine readable medium in accordance with claim 16 further configured to instruct a processor to:
   obtain detector samples at a plurality of collimator step positions that extend from the detector A-side to the detector B-side;
   determine a Z-ratio of the signals received from at least one detector A-side row and at least one detector B-side row; and
   normalize the determined Z-ratios utilizing a Batwing function.

18. A machine readable medium in accordance with claim 17 further configured to instruct a processor to:
   generate the target beam positions independently of the Z-ratios by selecting the smallest collimator aperture where the step-ratio does not exceed a predetermined sensitivity function; and
   select the target beam positions having normalized ratios that do not exceed a predefined limit.

19. A machine readable medium in accordance with claim 16 further configured to instruct a processor to:
   determine a detector A-side and a detector B-side target beam position using a first detector row and a second detector row that is different than the first detector row;
   generate a plurality of Z-ratio curves for the detector A-side and the detector B-side utilizing the first and second detector rows.

20. A machine readable medium in accordance with claim 19 further configured to instruct a processor to:
   determine a minimum value for each generated Z-ratio curve;
   determine a maximum value for each generated Z-ratio curve; and
   determine an operating point where each Z-ratio curve intersects with at least one the detector A-side target beam position and the detector B-side target beam position.

21. A machine readable medium in accordance with claim 20 further configured to instruct a processor to:
   determine a margin for each Z-ratio curve;
   select a detector A-side Z-ratio curve having the largest margin;
   select a detector B-side Z-ratio curve having the largest margin; and
   utilize the selected Z-ratio curves and corresponding detector channels and rows to position the collimator cams and X-ray beam during normal patient scanning.

* * * * *